US012569145B2

(12) United States Patent
Mensch et al.

(10) Patent No.: US 12,569,145 B2
(45) Date of Patent: Mar. 10, 2026

(54) SYSTEM AND METHOD FOR DETERMINING BODY CORE TEMPERATURE

(71) Applicant: Robert Bosch GmbH, Stuttgart (DE)

(72) Inventors: Beatrix Mensch, Illertissen (DE); Thomas Rocznik, Mountain View, CA (US); Christian Peters, Sunnyvale, CA (US); Seow Yuen Yee, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 956 days.

(21) Appl. No.: 16/956,735

(22) PCT Filed: Dec. 20, 2018

(86) PCT No.: PCT/US2018/066948

§ 371 (c)(1),
(2) Date: Jun. 22, 2020

(87) PCT Pub. No.: WO2019/133449

PCT Pub. Date: Jul. 4, 2019

(65) Prior Publication Data

US 2021/0121071 A1 Apr. 29, 2021

Related U.S. Application Data

(60) Provisional application No. 62/610,593, filed on Dec. 27, 2017.

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/7225* (2013.01); *G01K 13/20* (2021.01); *G16H 40/60* (2018.01);
(Continued)

(58) Field of Classification Search
CPC ......... A61B 5/01; A61B 5/7225; A61B 8/488; A61B 2562/0271; A61B 2562/028;
(Continued)

(56) References Cited

U.S. PATENT DOCUMENTS 3,776,040 A * 12/1973 Gould, III .............. G01K 13/20
338/195
5,816,706 A 10/1998 Heikkila et al.
(Continued)

FOREIGN PATENT DOCUMENTS

CA 2633419 A1 * 6/2007 ........... A61B 5/0031
CN 206379583 U * 8/2017
(Continued)

OTHER PUBLICATIONS

Cho, J., et al. "Evaluation of contacts for a MEMS thermal switch." Journal of Micromechanics and Microengineering 18.10: 105012. (Year: 2008).*
(Continued)

*Primary Examiner* — Devin B Henson
(74) *Attorney, Agent, or Firm* — Maginot, Moore & Beck LLP

(57) ABSTRACT

A temperature sensing system includes an insulator having a thermal resistance that is controllable from a first thermal resistance to a second thermal resistance, and at least one temperature sensor operable to sense temperature at first and second sides of the insulator. A processor is configured to control the thermal resistance of the insulator to change from the first thermal resistance to the second thermal resistance.

7 Claims, 8 Drawing Sheets

(51) Int. Cl.

| | | |
|---|---|---|
| *G01K 13/20* | (2021.01) | |
| *G16H 40/60* | (2018.01) | |
| *G16H 50/30* | (2018.01) | |
| *A61B 8/00* | (2006.01) | |

(52) U.S. Cl.
CPC .............. *G16H 50/30* (2018.01); *A61B 8/488* (2013.01); *A61B 2562/0271* (2013.01); *A61B 2562/028* (2013.01); *A61B 2562/18* (2013.01)

(58) Field of Classification Search
CPC .... A61B 2562/18; G16H 50/30; G16H 40/60; G01K 13/20
See application file for complete search history.

(56) References Cited

U.S. PATENT DOCUMENTS

| | | | | |
|---|---|---|---|---|
| 10,750,951 B1 * | 8/2020 | Prachar | .................. | G01K 13/20 |
| 2011/0051776 A1 * | 3/2011 | Bieberich | .............. | G01K 13/20 |
| | | | | 600/549 |
| 2013/0018411 A1 * | 1/2013 | Collings | .............. | A61B 17/282 |
| | | | | 606/205 |
| 2013/0331728 A1 | 12/2013 | Sun et al. | | |

FOREIGN PATENT DOCUMENTS

| | | | | | |
|---|---|---|---|---|---|
| DE | 3638943 C2 * | 4/1993 | ............. | H01H 85/10 |
| EP | 2567658 A1 * | 3/2013 | ......... | A61B 10/0233 |
| JP | 2009-236624 A | 10/2009 | | |
| JP | 2012-073128 A | 4/2012 | | |
| JP | 2013-170907 A | 9/2013 | | |
| KR | 20160143608 A | * | 12/2016 | ............... | A61B 5/01 |

OTHER PUBLICATIONS

International Search Report and Written Opinion corresponding to PCT Application No. PCT/US2018/066948, mailed Apr. 18, 2020 (10 pages).

Kitamura, K., et al., "Development of a New Method for the Noninvasive Measurement of Deep Body Temperature Without a Heater," Medical Engineering & Physics, vol. 32, 2010, pp. 1-6, Elsevier Ltd. 2009.

Huang, M. et al., "Theoretical Simulation of the Dual-Heat-Flux Method in Deep Body Temperature Measurements," 32nd Annual International Conference of the IEEE EMBS, pp. 561-564. IEEE 2010.

Huang, M. et al., "Improvement of the Dual-heat-flux Method for Deep Body Temperature Measurement Based on a Finite Element Model," 35th Annual International Conference of the IEEE EMBS, pp. 1202-1205. IEEE 2013.

Huang, M. et al., "Structural Optimization of a Wearable Deep Body Thermometer: From Theoretical Simulation to Experimental Verification," Journal of Sensors, vol. 2016, Article ID 4828093, 7 pages. Hindawi Publishing Corp. 2016.

Feng, J. et al., "Development of an Improved Wearable Device for Core Body Temperature Monitoring Based on the Dual Heat Flux Principle," Physiological Measurement, vol. 38 (2017), pp. 652-668. Institute of Physics and Engineering in Medicine, Mar. 17, 2017.

* cited by examiner

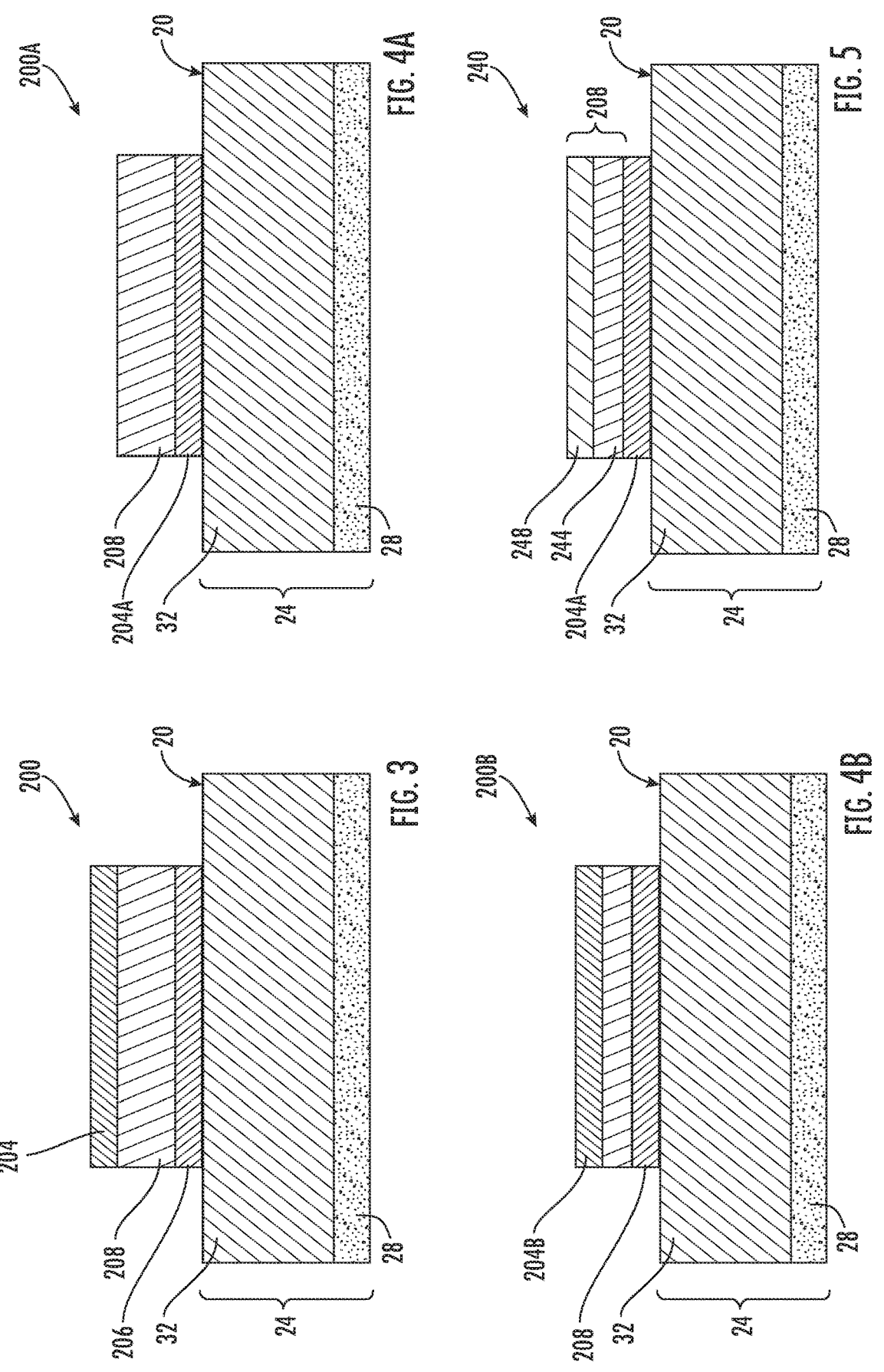

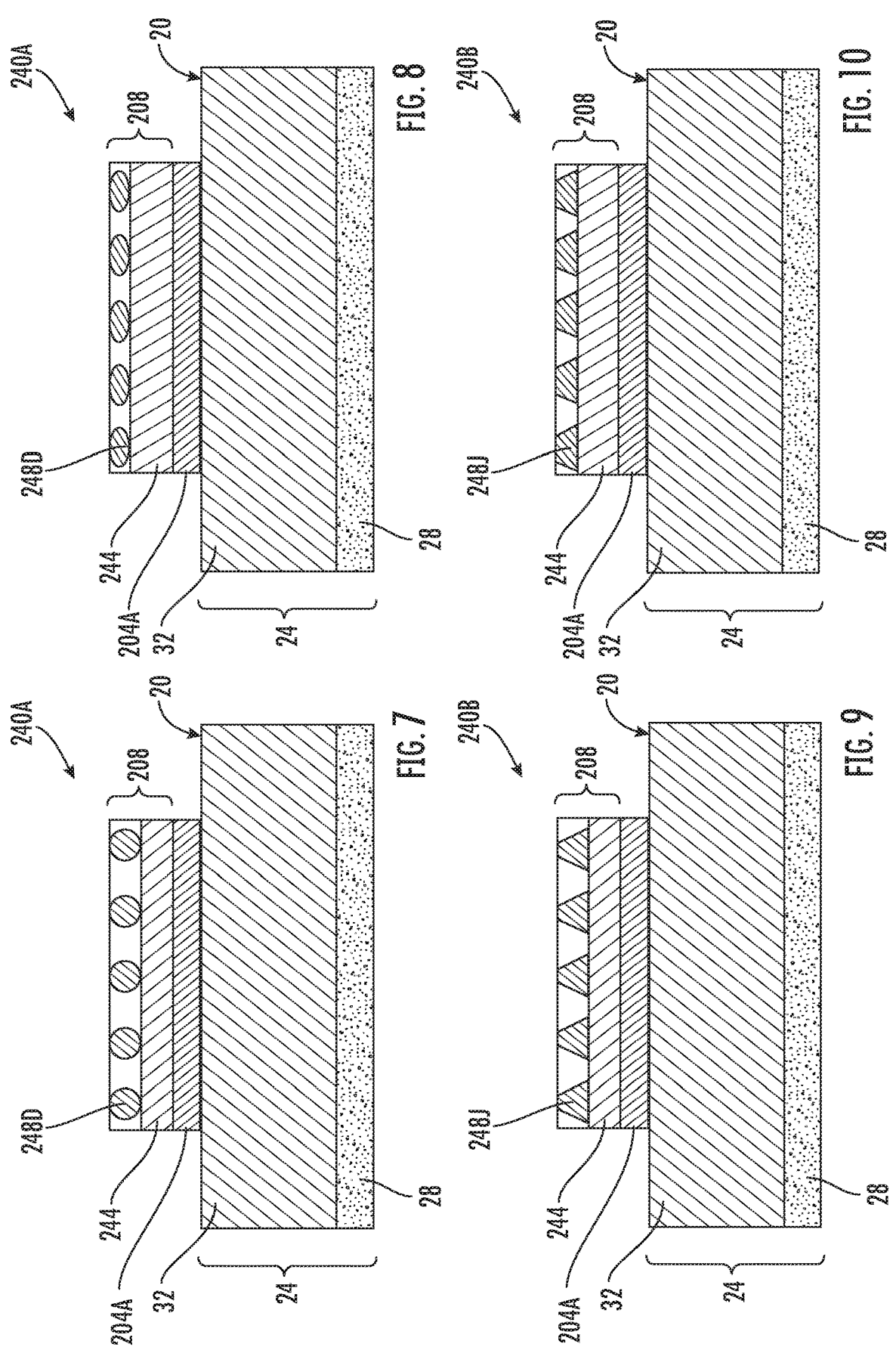

SYSTEM AND METHOD FOR DETERMINING BODY CORE TEMPERATURE

CLAIM OF PRIORITY

This application is a 35 U.S.C. § 371 National Stage Application of PCT/US2018/066948, filed on Dec. 20, 2018, which claims priority to U.S. Provisional Application Ser. No. 62/610,593 entitled "System and Method for Determining Core Body Temperature" and filed on Dec. 27, 2017, the disclosures of which are incorporated herein by reference in their entirety.

TECHNICAL FIELD

This disclosure relates generally to temperature sensors, and more particularly to temperature sensors for detecting core body temperature.

BACKGROUND

The body core temperature of a human or animal is an important vital sign used to diagnose, treat, and monitor a number of health conditions. Accurate determination of body core temperature is crucial in diagnosis and treatment of medical conditions, while inaccurate determination of body core temperature can compromise patient health.

Conventional methods of determining body core temperature include inserting a temperature sensor internally into the body, which is invasive and can cause hygienic and biohazard issues. External methods of determining body core temperature typically suffer from reduced accuracy of the measurements, which, as noted above, reduces the usefulness of the body core temperature measurement.

In particular, the surface temperature of the body is not the same as the body core temperature because the outer surface of a human or animal's skin exchanges heat with the subject's surroundings. The rate at which the skin exchanges heat with the surroundings and the relationship between the body core temperature within the body and the temperature of the external surface of the skin varies by the individual, the location on the body, and the external conditions. As a result, it is difficult to accurately determine the body core temperature based on the temperature of the external surface of the skin.

What is needed therefore is a system and method to determine body core temperature that is minimally invasive. Moreover, a system and method that accurately determines the body core temperature from an external measurement would also be beneficial.

SUMMARY

A temperature sensing system includes an insulator having a thermal resistance that is controllable from a first thermal resistance to a second thermal resistance, and at least one temperature sensor operable to sense temperature at first and second sides of the insulator. A processor is configured to control the thermal resistance of the insulator to change from the first thermal resistance to the second thermal resistance.

In some embodiments, the processor is further configured to determine a subject core body temperature based on first detected temperatures from the at least one temperature sensor on the first and second sides of the insulator when the insulator is at the first thermal resistance, and second detected temperatures from the at least one temperature sensor on the first and second sides of the insulator when the insulator is at the second thermal resistance.

In another embodiment, the processor is further configured to generate an output of the determined subject core body temperature as one of a perceptible output and an output signal.

In yet another embodiment, the determination of the subject core body temperature is determined according to the equation:

$$T_B = T_1 + \frac{(T_1 - T_2)(T_1 - T_3)}{K(T_2 - T_4) - (T_1 - T_2)},$$

wherein:

$T_B$ is the subject core body temperature;

$T_1$ is the first detected temperature at the first side of the insulator;

$T_2$ is the second detected temperature at the first side of the insulator;

$T_3$ is the first detected temperature at the second side of the insulator;

$T_4$ is the second detected temperature at the second side of the insulator; and K is the first thermal resistance divided by the second thermal resistance.

In some embodiments, the at least one temperature sensor includes a Doppler sensor.

In further embodiments, the at least one temperature sensor includes a first temperature sensor on the first side of the insulator, and a second temperature sensor on the second side of the insulator.

In another embodiment of the temperature sensing system, the insulator includes at least one compressible element and at least one biasing structure. The processor is configured to operate the biasing structure to selectively exert a biasing force that compresses the at least one compressible element.

In some embodiments, the at least one biasing structure includes a piezoelectric element.

In another embodiment according to the disclosure, the insulator includes at least one MEMS switch configured, in a closed state, to conduct heat between the first and second sides of the insulator.

The insulator may, in some embodiments, include a plurality of fuses and a plurality of structures with low thermal conductivity, the plurality of fuses and plurality of structures with low thermal conductivity arranged in parallel with one another.

In another embodiment according to the disclosure, a method of operating a temperature sensing system comprises: controlling a thermal resistance of an insulator of the temperature sensing system to change from a first thermal resistance to a second thermal resistance; sensing a temperature of a first side of the insulator and a second side of the insulator when the insulator is at the first thermal resistance and when the insulator is at the second thermal resistance; and determining a subject core body temperature based on the sensed temperatures.

In one embodiment, the method further comprises generating an output of the determined subject core body temperature as one of a perceptible output and an output signal.

In a further embodiment according to the disclosure, the determination of the subject core body temperature is determined according to the equation:

$$T_B = T_1 + \frac{(T_1 - T_2)(T_1 - T_3)}{K(T_2 - T_4) - (T_1 - T_2)},$$

wherein:

$T_B$ is the subject core body temperature;

$T_1$ is a first temperature reading at the first side of the insulator when the insulator is at the first thermal resistance;

$T_2$ is a second temperature reading at the first side of the insulator when the insulator is at the second thermal resistance;

$T_3$ is a third temperature reading at the second side of the insulator when the insulator is at the first thermal resistance;

$T_4$ is a fourth temperature reading at the second side of the insulator when the insulator is at the second thermal resistance; and K is the first thermal resistance divided by the second thermal resistance.

In another embodiment of the method, the operating of the insulator to change the thermal resistance includes operating at least one piezoelectric element to exert a biasing force that compresses at least one compressible element so as to change the thermal resistance of the insulator.

In some embodiments, the operating of the insulator to change the thermal resistance includes activating at least one MEMS switch in the insulator, the MEMS switch configured, in a closed state, to conduct heat between the first and second sides of the insulator.

In a further embodiment, the operating of the insulator to change the thermal resistance includes applying an electrical charge to at least one fuse in the insulator so as to at least partially destroy the at least one fuse and change the thermal conductivity of the insulator.

In one embodiment according to the disclosure, a temperature probe comprises an insulator having a thermal resistance, the insulator configured such that the thermal resistance is controllable from a first predetermined value to a second predetermined value; and at least one temperature sensor configured to sense a first temperature at a first side of the insulator and a second temperature at a second opposite side of the insulator.

In yet another embodiment of the temperature probe, the insulator includes at least one compressible element and at least piezoelectric element, and the piezoelectric element is configured to selectively exert a biasing force that compresses the at least one compressible element.

In some embodiments, the insulator includes at least one MEMS switch configured, in a closed state, to conduct heat between the first and second sides of the insulator.

In further embodiments, the insulator includes a plurality of fuses and a plurality of structures with low thermal conductivity, the plurality of fuses and plurality of structures with low thermal conductivity arranged in parallel with one another.

BRIEF DESCRIPTION OF THE DRAWINGS

FIG. 3 is a schematic illustration of a temperature probe arrangement in which a layer of variable thermal resistance is interposed between two temperature sensors.

FIG. 4A is a schematic illustration of a temperature probe arrangement in which a layer of variable thermal resistance is positioned on a Doppler sensor.

FIG. 4B is a schematic illustration of a temperature probe arrangement in which a layer of variable thermal resistance is positioned between a Doppler sensor and the skin.

FIG. 5 is a schematic illustration of the temperature probe arrangement of FIG. 4A in which the layer of variable thermal resistance positioned on a Doppler sensor includes a piezoelectric element and a plurality of compressible elements.

FIG. 7 is a schematic illustration of the temperature probe arrangement of FIG. 5, in which the compressible elements include a plurality of cylindrical elements, in a minimally compressed or uncompressed state.

FIG. 8 is a schematic illustration of the temperature probe arrangement of FIG. 7, in which the compressible elements are in a compressed state.

FIG. 9 is a schematic illustration of the temperature probe arrangement of FIG. 5, in which the compressible elements include a plurality of trapezoidal prisms, in a minimally compressed or uncompressed state.

FIG. 10 is a schematic illustration of the temperature probe arrangement of FIG. 9, in which the compressible elements are in a compressed state.

DETAILED DESCRIPTION

For the purposes of promoting an understanding of the principles of the embodiments described herein, reference is now made to the drawings and descriptions in the following written specification. No limitation to the scope of the subject matter is intended by the references. This disclosure also includes any alterations and modifications to the illustrated embodiments and includes further applications of the principles of the described embodiments as would normally occur to one skilled in the art to which this document pertains.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The terms "comprising," "including," "having," and the like, as used with respect to embodiments of the disclosure, are synonymous. As used herein, the term "approximately" refers to values that are within ±20% of the reference value.

Figure 1:
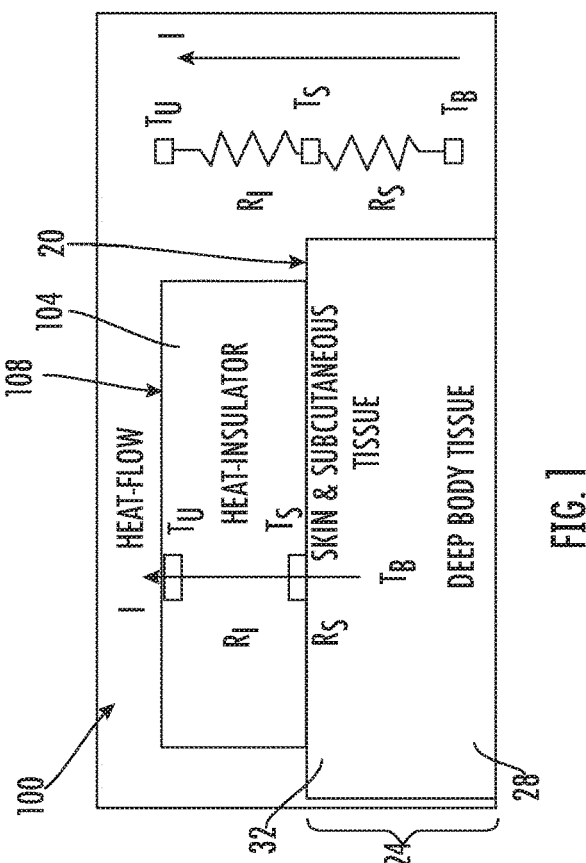
FIG. 1 is a schematic illustration of heat flow through the skin and an attached Doppler sensor.

As illustrated in FIG. 1, human or animal (collectively referred to herein as a "subject") body core temperature can be determined with a Doppler sensor 100 placed on the skin surface 20 of the body 24 using the dual heat flux method. In the dual heat flux method, two temperature sensor readings are used, $T_U$ and $T_S$, one of which is taken on each side of an insulating layer 104 of the sensor 100. The sensor 100 is placed on the skin surface 20, so that the temperature $T_S$ between the skin surface 20 and the insulating layer 104 is measured, as well as the temperature $T_U$ on the top surface 108 of the insulating layer 104. It is assumed that there is a constant vertical heat flow I from the body core or deep body tissue 28 to the top surface 108 of the sensor 100. Thus the heat flow through the sensor 100 is the same as the heat flow through the skin and subcutaneous tissue layer 32 below the sensor. The heat flow through the Doppler sensor can be calculated based on Fourier's law:

$$I = \frac{T_S - T_U}{R_I},$$

wherein:

I=heat flow or heat transfer rate $T_S$=temperature between the skin 32 and the insulating layer 104

$T_U$=temperature at the top surface 108 of the insulating layer 104, and $R_I$=thermal resistance of the insulating layer 104.

Similarly, the heat flow through the skin layer 32 below the sensor 100 can be calculated as follows:

$$I = \frac{T_B - T_S}{R_S},$$

wherein:

$T_B$ body core temperature of the deep body tissue 28 and $R_S$=thermal resistance of the skin layer 32.

Since the heat flow I through the sensor 100 is the same as the heat flow I through the skin layer 32 below the sensor 100, these two equations can be combined and the body core temperature $T_B$ can be calculated with the following equation:

$$T_B = T_S + \frac{(T_S - T_U)R_S}{R_I}.$$

The body core temperature $T_B$ can then be determined if the thermal resistance $R_S$ of the skin layer 32 is known. However, the thermal properties, in particular the thermal resistance $R_S$, of human skin are very difficult to accurately determine. In addition, there is a wide variance in the thermal properties for each individual human or animal and for different locations on the body. Thus, a generic approximation of the thermal resistance $R_S$ of the skin layer 32 cannot be used to provide an accurate determination of the body core temperature $T_B$.

Figure 2:
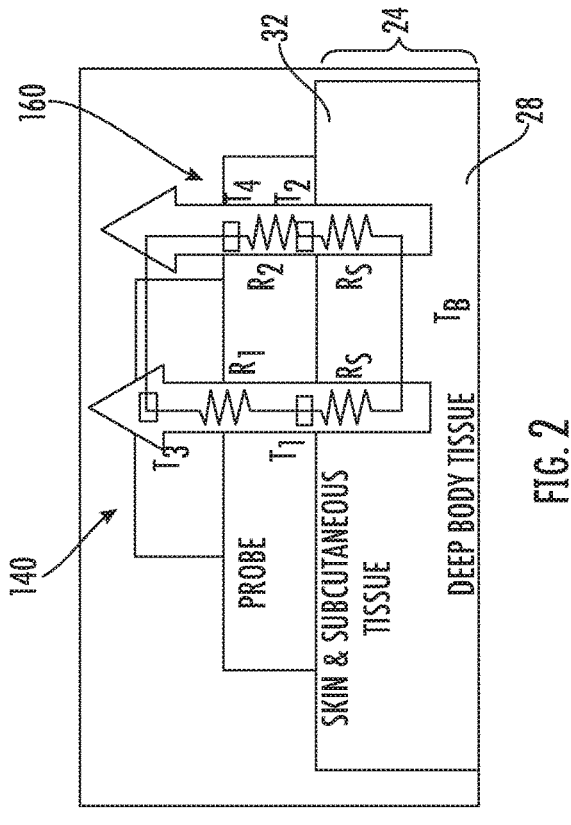
FIG. 2 is a schematic illustration of two sensors attached to the skin and the heat flow through the skin and the sensors.

To eliminate the thermal resistance of the skin from the determination, a system is illustrated in FIG. 2 having two sensors 140, 160 with different heights and therefore different thermal resistance values $R_1$, $R_2$. The two sensors 140, 160 are placed on the skin 32 close to one another and read different temperatures $T_1$, $T_2$ due to the different thermal resistance values $R_1$, $R_2$ of the sensors 140, 160. In addition, it is assumed that since the sensors 140, 160 are placed close to one another, the thermal resistance $R_S$ of the skin layer 32 below each of the sensors 140, 160 is the same. The body core temperature $T_B$ can then be calculated with the following equations:

$$T_B = T_1 + \frac{(T_1 - T_3)R_S}{R_1}$$

and $$T_B = T_2 + \frac{(T_2 - T_4)R_S}{R_2},$$

wherein $T_1$ and $T_2$ are the lower or skin surface temperatures read by the first and second sensors 140, 160, respectively, and $T_3$ and $T_4$ are the upper surface temperatures on the opposite side of the insulating layers of the respective first and second sensors 140, 160.

The last two equations can be combined to the following equation:

$$T_B = T_1 + \frac{(T_1 - T_2)(T_1 - T_3)}{K(T_2 - T_4) - (T_1 - T_2)},$$

wherein $$K = \frac{R_1}{R_2}.$$

Therefore the body core temperature $T_B$ can be determined without knowing the thermal properties, in particular the thermal resistance ($R_S$), of the skin layer 32. However, for an accurate determination of the body core temperature $T_B$, the thermal resistance values $R_1$, $R_2$ of both sensors 140, 160 must be known or the factor K must be determined by calibrating the sensors 140, 160. Moreover, the sensors must be close enough to one another that the assumption that the skin thermal resistance is equal remains valid.

FIG. 3 illustrates an embodiment according to the disclosure of a temperature probe 200 having temperature sensors 204, 206 on opposite sides of an insulating layer 208 that has a thermal resistance that can be changed between at least two known values. As such, the initial temperatures $T_1$ and $T_3$ can be taken with a known thermal resistance $R_1$, while the second temperature measurements $T_2$ and $T_4$ can be taken with a known thermal resistance $R_2$. Thus, all parameters for the deep core body temperature are known, and the deep core body temperature can be calculated with high accuracy for the subject using the dual heat flux method. The temperature sensors 204, 206 may be, for example, thermocouples, resistance temperature detectors (RTDs), negative temperature coefficient (NTC) thermistors, diode-based semiconductor integrated circuit temperature sensors, or any other desired temperature sensor.

FIG. 4A illustrates an embodiment according to the disclosure of a temperature probe 200A in which a Doppler sensor 204A is positioned between the skin 32 and an insulating layer 208 having a thermal resistance that can be changed between at least two known values. In the embodiment of FIG. 4A, the insulating layer 208 is positioned on the side of the Doppler sensor 204 opposite the surface 20 of the skin 32. The Doppler sensor 204A provides temperature readings at both the skin surface 20 and the opposite side of the insulating layer 208. The Doppler sensor may include, for example, sensor circuits or temperature leads at both the skin surface 20 and at the opposite side of the insulating layer 208.

In another embodiment of a temperature probe 200B, illustrated in FIG. 4B, the insulating layer 208 is interposed between the surface 20 of the skin 32 and the Doppler sensor 204B. Although the temperature probes disclosed below are all described with the insulating layer on the side of the Doppler sensor opposite the surface of the skin, as in FIG. 4A, the reader should appreciate that all disclosed temperature probes can also be configured as in FIG. 3 with temperature sensors 204, 206 above and below the insulating layer, or as in FIG. 4B such that the insulating layer is interposed between the surface of the skin and the Doppler sensor 204B.

FIG. 5 illustrates an embodiment of the temperature probe 240 in which the insulating layer 208 includes a biasing structure, for example a piezoelectric element 244, and at least one elastic compressible element 248 arranged in a layer above the piezoelectric element 244. The compressible element 248 is configured such that expansion of the piezoelectric element 244 causes a non-negligible compression at least a portion of the compressible element 248 so as to alter the thermal resistance of the compressible element 248. Conversely, upon contraction of the piezoelectric element 244, at least a portion of the compressible element 248 expands elastically into the space vacated by the contraction of the piezoelectric element 244.

Figure 6:
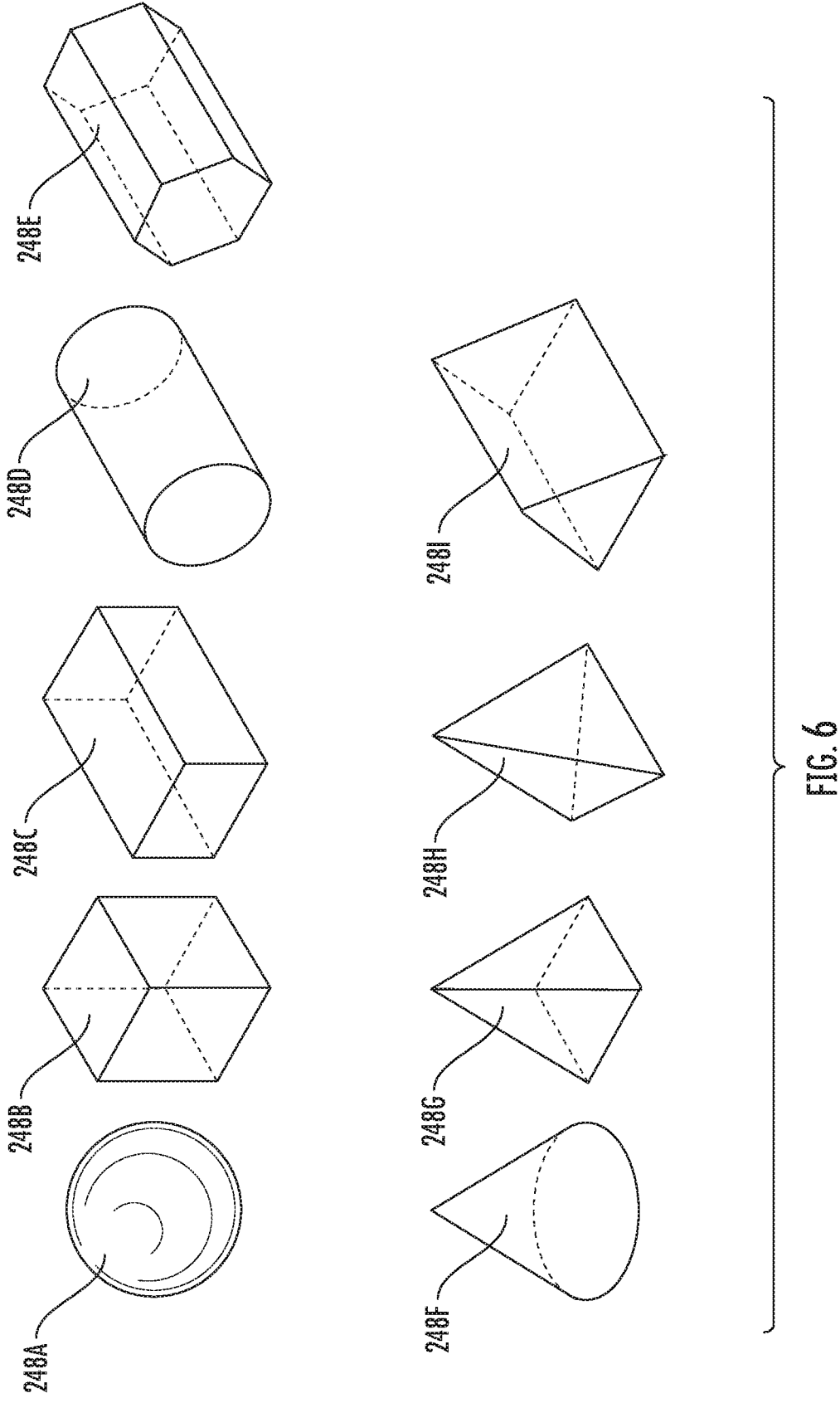
FIG. 6 shows a plurality of potential shapes for the plurality of compressible elements of FIG. 5.

As illustrated in FIG. 6, the compressible elements 248 can be, for example, spheres 248A, cubes 248B, cuboids 248C, cylinders 248D, hexagonal prisms 248E, cones 248F, square or triangular pyramids 248G, 248H, respectively, triangular prisms 248I, any other suitable prism or shape, or any combination of the above described elements.

The reader should appreciate that the embodiments with compressible elements are not limited to piezoelectric elements as the biasing structure. For example, in some embodiments, the biasing structure may include to change the dimension of the element, for example the Joule effect, a pressurized bladder or air or another fluid, an electric motor, an electromagnet and corresponding magnetic structure, or any other desired controllable biasing structure.

FIGS. 7 and 8 illustrate an example of a temperature probe 240A with cylindrical compressible elements 248D. The temperature probe 240A has a Doppler sensor 204A and a thermal insulator 208 comprising a piezoelectric element and a plurality of compressible cylinders 248D arranged in a layer on the piezoelectric element 244.

As illustrated in FIGS. 7 and 8, the piezoelectric element 244 is configured such that applying a voltage to the piezoelectric element 244 causes the piezoelectric element 244 to expand, while the overall height h of the temperature probe 240A remains constant. As a result, the expansion of the piezoelectric element 244 compresses the compressible elements 248D. After expansion of the piezoelectric element 244, the contact surface of the compressible elements 248D with the top of the piezoelectric element 244 and the top of the temperature probe 240A increases. This results in a decrease of the thermal resistance of the compressible elements 248D, thereby reducing the overall thermal resistance of the combined stack of the piezoelectric element 244 and the compressible elements 248D.

After the voltage is removed from the piezoelectric element 244, the piezoelectric element 244 contracts back to the position illustrated in FIG. 7, thereby allowing the compressible elements 248D to elastically expand to their initial states. As a result, the temperature probe 240A can then be used to take another set of temperature readings.

In some embodiments, the compressible elements 248D may be compressed in an initial state and the piezoelectric elements 248D may be expanded in the initial state (i.e. in the state of FIG. 8). The piezoelectric element 244 may be configured to contract, thus allowing the compressible elements to expand (to the state of FIG. 7). Thus, as used herein, the term "compressible elements" includes expandable elements that begin in a compressed state.

FIGS. 9 and 10 illustrate another embodiment of a temperature probe 240B in which the compressible elements are formed as trapezoidal prisms 248J arranged in a layer. As can be seen in FIG. 10, when compressed, the expansion of the piezoelectric element 244 causes the trapezoidal prisms 248J to have greater contact surfaces with the top of the piezoelectric element 244 and the top of the temperature probe 240B, thus decreasing the thermal resistance of the temperature probe 240B. Similarly to the temperature probe 240A, removing the voltage from the piezoelectric element 244 allows the trapezoidal prisms 248J to expand back to their initial state, as illustrated in FIG. 9, to enable the temperature probe to be reused.

Figure 11A:
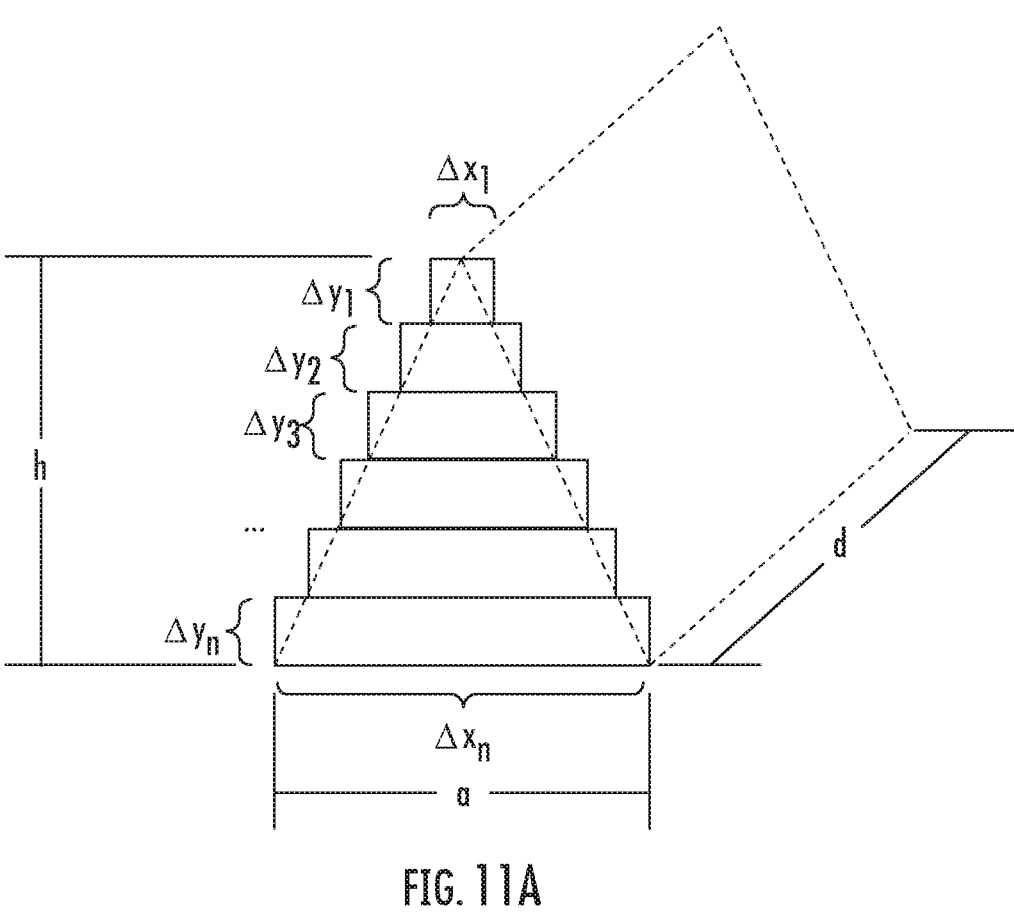
FIG. 11A illustrates a side view of a front perspective view a triangular prism for use in the temperature probe arrangement of FIG. 5 divided into n differential elements.
Figure 11B:
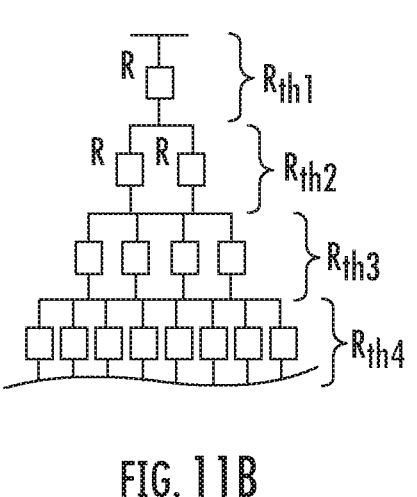
FIG. 11B schematically illustrates the differential elements of the triangular prism of FIG. 11A depicting the thermal resistances of the differential elements.
Figure 11C:
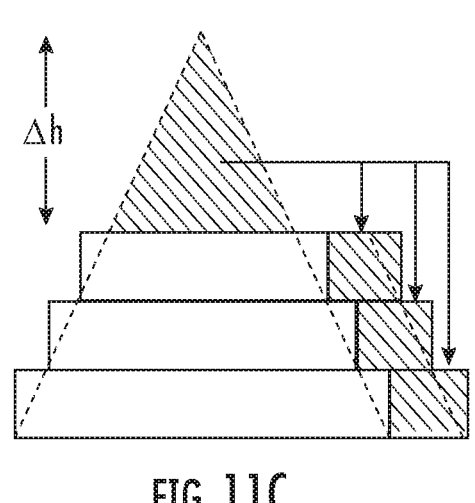
FIG. 11C illustrates a side view of the triangular prism of FIG. 11A compressed by a distance of compression $\Delta h$ and showing the compressed portion being conceptually added to the remaining differential segments in the compressed prism.

FIGS. 11A-11C illustrate the relationship between compression and thermal resistance of a triangular prism. An integral approximation is used to calculate the shape of the compressed prism and the resulting thermal resistance as follows. The thermal resistance of a cuboid can be calculated with the following equation:

$$R_{th} = \frac{l}{k \cdot A},$$

wherein:

$R_{th}$=thermal resistance, l=length, k=thermal conductivity, and

A=area.

To calculate the thermal resistance of a triangular prism, the prism is divided in n cuboids, as illustrated in FIG. 11A, each of which has a height $\Delta y$, a width $\Delta x$, and a depth d (FIG. 11A). The thermal resistance $R_{th,A}$, $R_{th,B}$, . . . $R_{th,n}$ of each respective cuboid is calculated using the equation:

$$R_{th,n} = \frac{\Delta y}{k \cdot A_n},$$

where k is a thermal conductivity constant and $A_n$=d (prism depth)·$\Delta x_n$ (width of the segment).

The total thermal resistance $R_{th}$ of the triangular prism 300 is the sum of all cuboids $R_{th}=\Sigma_1{}^n R_{th,n}$ (FIG. 11B).

For the calculation of the thermal resistance of a compressed triangular prism, illustrated in FIG. 11C, the estimated values change due to the compression of the prism. Since the triangular prism is compressed, the height of the prism is reduced by $\Delta h$, and the prism now has fewer segments of height $\Delta y$. The volume of the prism portions within the distance of compression is added to the lower divisions, as illustrated in FIG. 11C, so that the total volume of the prism remains the same.

For n→∞ and no compression, the thermal resistance calculated according to this equation would be infinity. Thus, the triangular prism must be at least slightly compressed for the differential model to work. In this illustrative example, for the so-called "uncompressed" calculation of the thermal resistance, the prism is considered to be approximately 10% compressed in the initial state. As the distance of compression $\Delta h$ increases, the thermal resistance decreases.

To change the thermal resistance of the temperature probe 200, 200A, 200B, 240, 240A, 240B by a certain percentage, the ratios the thermal resistance for each layer must be known. For instance, if the thermal resistance of the triangular prisms ($R_{th,p}$) is three times larger than the thermal resistance of the piezoelectric element and the Doppler sensor together ($R_{th,s}$), the thermal resistance of the compressed elements must be 66% smaller to reach a total decrease of 50% of the thermal resistance of the whole stack. As illustrated in the following calculation, this means the elements are compressed by about 40% to achieve the 50% decrease of thermal resistance.

In the uncompressed state:

$$R_{th,s}=R_{th,1} \text{ and } R_{th,p1}=3 \cdot R_{th,1}$$

$$R_{th,tot1}=R_{th,p1}+R_{th,s}=4 \cdot R_{th,1}.$$

In the compressed state:

$$R_{th,p2}=33\% * 3 \cdot R_{th,1}=R_{th,1}$$

$$R_{th,tot2}=R_{th,p2}+R_{th,s}=2 \cdot R_{th,1}.$$

Thus:

$$R_{th,tot2} = \frac{1}{2} \cdot R_{th,tot1}.$$

Figure 12:
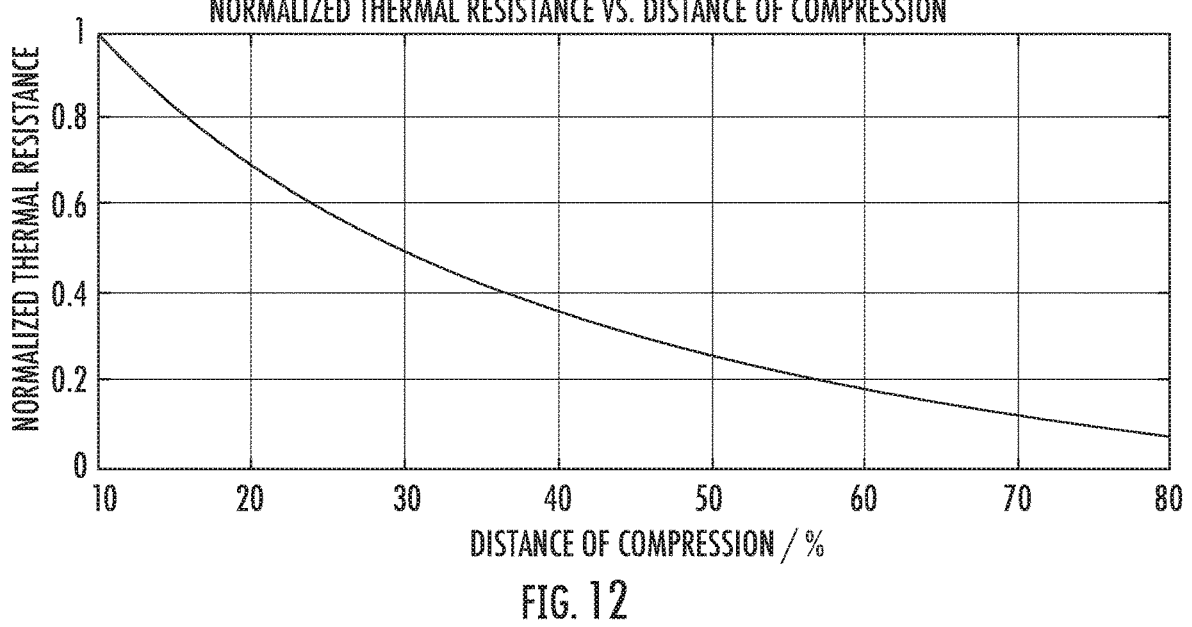
FIG. 12 is a graph of the normalized thermal resistance of pyramids over a range of compression percentages.

In some embodiments, the thermal resistance of the compressible elements is several times larger (i.e. approximately 3 times larger to approximately 20 times larger) than the combined thermal resistance of the piezoelectric element and Doppler sensor. As a result, changing the thermal resistance of the compressible elements changes the thermal resistance of the temperature probe 200, 200A, 200B, 240, 240A, 240B by a relatively large amount, which enables the dual heat flux method to accurately determine the core body temperature based on the skin temperature. FIG. 12 illustrates a graph of the normalized thermal resistance of pyramids over a range of compression distances.

The compressible elements can be formed of any suitable compressible and flexible material. The compressible elements may be solid or hollow with air inside. In one embodiment, the compressible elements are formed of rubber or polymer. In another embodiment, the compressible elements are formed of a metal and one or more of rubber or polymer. In other embodiments, the compressible elements are formed of a compressible and flexible material coated with a metal coating.

While the embodiments above are described with reference to only one piezoelectric element, the reader should appreciate that, in other embodiments, the sensor may include a plurality of piezoelectric elements stacked on each other, arranged in an array, and/or arranged in parallel with one another.

Figures 13, 14:
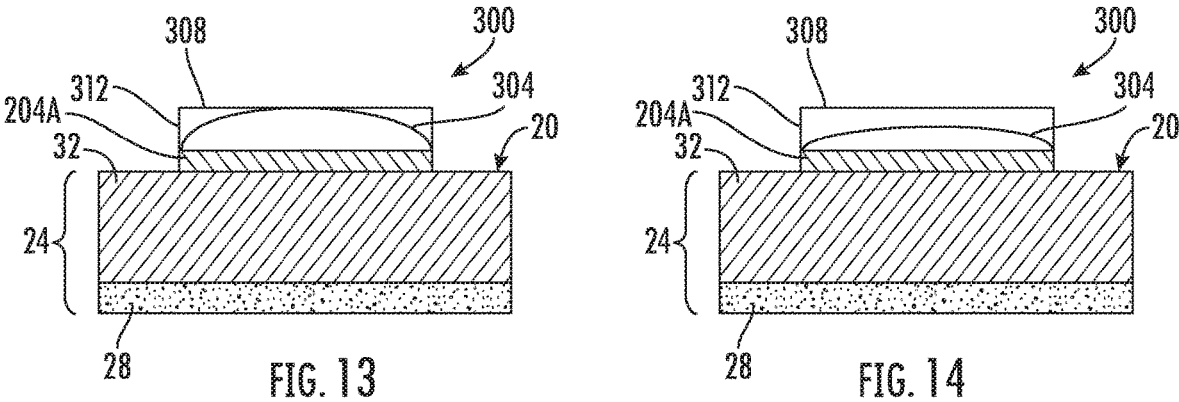
FIG. 13 is a schematic illustration of the temperature probe arrangement of FIG. 4A, in which the layer of variable thermal resistance includes a MEMS switch formed as a beam that produces a closed thermal connection.
FIG. 14 is a schematic illustration of the temperature probe arrangement of FIG. 13, in which the MEMS switch interrupts the thermal connection.

FIGS. 13 and 14 illustrate another embodiment of a temperature probe 300 for determining the body core temperature by sensing the temperature at the surface 20 of a subject's skin 24. The sensor includes a Doppler sensor 204A and a MEMS (micro-electro-mechanical system) switch 304 configured as the insulating layer positioned between the Doppler sensor 204A and the top 308 of the housing 312 of the temperature probe 300. The MEMS switch 304 is used to change the thermal resistance of the temperature probe 300 between a lower thermal resistance state, in which the MEMS switch 304 is in contact with the top 308 of the temperature probe 300 to form a thermal path between top 308 and bottom (FIG. 13), and a higher thermal resistance state, in which the MEMS switch 304 is not in contact with the top 308 of the temperature probe 300, and therefore has no thermal path (or a significantly more resistive thermal path through the air gap or the side walls) between top 308 and bottom of the temperature probe 300 (FIG. 14).

To ensure that the MEMS switch 304 adequately changes the thermal resistance of the temperature probe 300 when the switch interrupts thermal contact between the top and the bottom wall, the side walls of the housing 312 have a high thermal resistance. The MEMS switch 304 has a relatively low thermal resistance compared to the side walls of the housing 312. In some embodiments, for example, the MEMS switch 304 includes a flexible metal coating.

The MEMS switch 304 may include any suitable material that can produce and interrupt contact between the top and the bottom wall, for instance an electroactive polymer that moves upon application or removal of an electrical voltage. In other embodiments, the MEMS switch 304 may be electromagnetic, piezoelectric, thermally activated or electrostatic.

Figure 15:
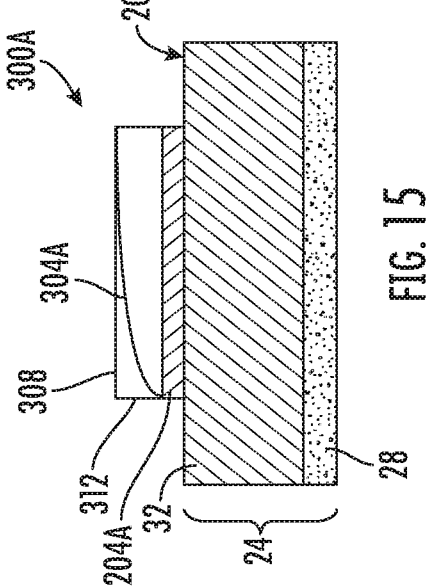
FIG. 15 is a schematic illustration of the temperature probe arrangement of FIG. 4A, in which the layer of variable thermal resistance includes a MEMS switch formed as a flap that produces a closed thermal connection.
Figure 16:
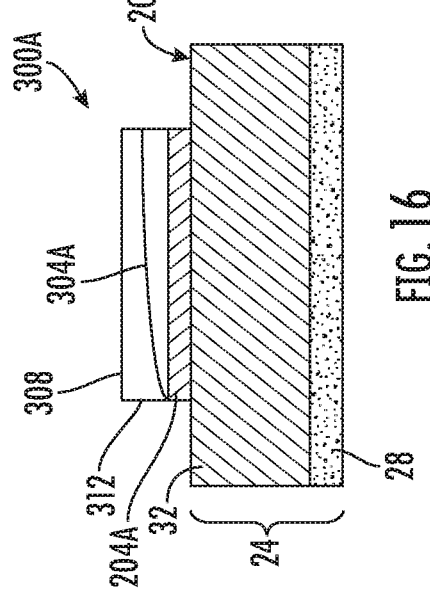
FIG. 16 is a schematic illustration of the temperature probe arrangement of FIG. 15, in which the MEMS switch interrupts the thermal connection.

FIGS. 15 and 16 illustrate another embodiment of a temperature probe 300A. The temperature probe 300A is substantially identical to the temperature probe 300 illustrated in FIGS. 12 and 13, except the MEMS switch 304A is formed as a flap instead of a beam. The reader should appreciate that the MEMS switch may have any suitable shape.

Figure 17:
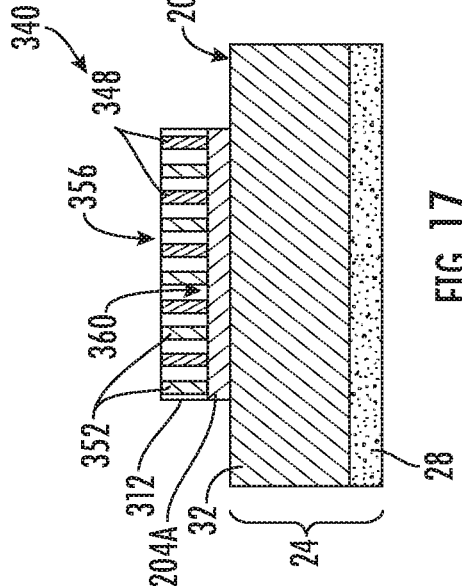
FIG. 17 is a schematic illustration of the temperature probe arrangement of FIG. 4A, in which the layer of variable thermal resistance includes a plurality of fuses.
Figure 18:
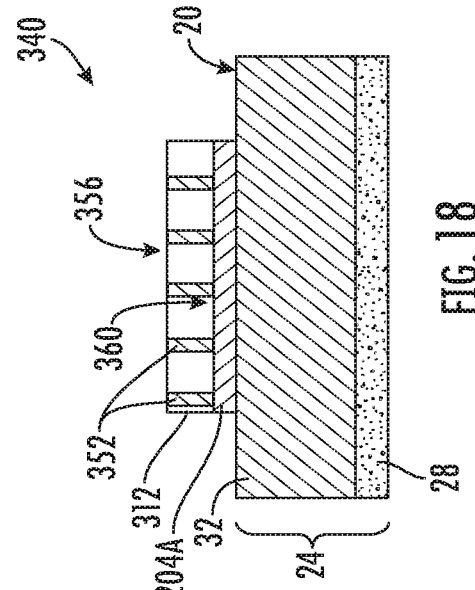
FIG. 18 is a schematic illustration of the temperature probe arrangement of FIG. 17, in which the plurality of fuses have been destroyed.

FIGS. 17 and 18 illustrate another embodiment of a temperature probe 340 for detecting the core body temperature of a human or animal. The temperature probe 340 includes an insulating layer 344 comprising fuses 348 and elements 352 with low thermal conductivity relative to the fuses arranged on the Doppler sensor 204A. The fuses 348 provide a thermal connection between the top 356 and the bottom 360 of the insulating layer 344 (see FIG. 17). Between two temperature measurements, at least one of the fuses 348 is completely or partially removed or destroyed. Thus, there is less thermal connection between the top 356 and bottom 360 of the insulating layer 344, and the thermal resistance of the insulating layer 344 therefore increases. In embodiments in which the fuses 348 are partially destroyed, the process can be repeated until all fuses 348 are destroyed, and the temperature probe 340 is then disposed of or the insulating layer 344 is replaced.

The reader should appreciate that partially destroying the fuse 348 may refer to completely destroying a limited quantity of the fuses 348, or only partially destroying all or a subset of the fuses 348 so as to reduce the diameter of each fuse 348 and thereby increase the thermal resistance.

In one embodiment, the fuses 348 are partially destroyed by using fuses 348 having different thicknesses. To destroy the first amount of fuses 348, the current used is comparatively small. To destroy the fuses 348 having greater thickness, the current applied to the fuses is relatively greater. Advantageously, in such an embodiment all of the fuses 348 can be connected together.

In another embodiment, the fuses 348 are destroyed individually by applying current only to the fuses 348 that are desired to be destroyed. In such an embodiment, all fuses can be advantageously implemented at the same time.

Figure 19:
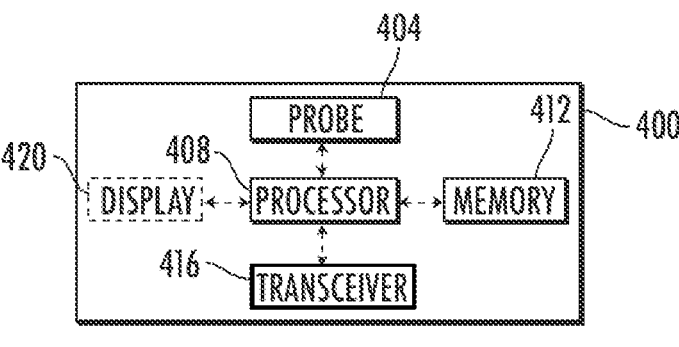
FIG. 19 is a schematic illustration of a temperature sensing system that incorporates the temperature probe arrangement of one of FIGS. 3-5, 7-10, and 13-18.

FIG. 19 is a schematic representation of a temperature sensing system 400. The temperature sensing system 400 includes a temperature probe 404 that has a layer with a variable thermal conductivity. The temperature probe 404 may, for example, comprise any of the temperature probes 200, 200A, 200B, 240, 240A, 240B, 300, 300A, 340 described above. The temperature probe 404 includes one or more temperature sensors configured to sense the temperature at the skin interface and on the side of the variable conductivity layer opposite the skin and to produce electronic signals representative of the sensed temperatures.

The temperature sensing system 400 also includes a processor 408 operably connected to a memory 412, and, in some embodiments, a transceiver 416 and/or a display 420. It will be recognized by those of ordinary skill in the art that a "processor" includes any hardware system, hardware mechanism or hardware component that processes data, signals or other information. The processor 408 may include a system with a central processing unit, multiple processing units, dedicated circuitry for achieving functionality, or other systems.

The memory 412 may be of any type of device capable of storing information accessible by the processor 408, such as write-capable memories, read-only memories, a memory card, ROM, RAM, hard drives, discs, flash memory, or other computer-readable medium. The memory 412 is configured to store program instructions that, when executed by the processor 408, enable the temperature sensing system 400 to determine the core temperature of a subject by taking two temperature measurements, between which the thermal conductivity of the temperature probe 404 is altered.

The transceiver 416 may include for example, one or more of a Wi-Fi® transceiver, a ZigBee® transceiver, a Z-Wave® transceiver, a Bluetooth® transceiver, a wireless telephony transceiver, and RF transceiver, or another transceiver suitable to send and receive communication signals to and from the temperature sensing system 400. In some embodiments, the transceiver may be configured to transmit the determined core body temperature to a computer, a nursing station, a portable electronic device such as a cellular telephone, tablet, or smart watch, or other desired electronic device.

The display 420 is configured to output a perceptible indication of the detected core body temperature. For instance, in one embodiment, the display may be a liquid crystal display (LCD), one or more light emitting diodes (LEDs), or another suitable display. In some embodiments, the temperature sensing system may have an audible output device, for example a speaker, instead of the display, to output the perceptible indicator as an audible output. In further embodiments, the perceptible output may be a haptic output produced by a vibrating or other haptic outputting device. In other embodiments, the temperature sensing system has no display, and is instead configured to output the determined core body temperature as an electronic signal via, for example, the transceiver or via a wired connection, rather than a perceptible output.

The temperature sensing system 400 may be formed as a single portable package with some or all the components 404, 408, 412, 416, and/or 420 integrated within a common housing (not shown). In other embodiments, the temperature probe 404 may be remote from the processor, and both the temperature probe and processor may include transceivers that communicate with one another so as to pass electronic signals between the temperature probe 404 and the processor 408. For example, in some embodiments, the processor and memory may be integrated in another electronic device, for example a computer, a nursing station, or a portable electronic device such as a cellular telephone, tablet, or smart watch, that communicates with the temperature probe via the transceivers. In some embodiments, the temperature probe and/or the temperature sensing system may include a battery (not shown) to provide electric power to the components in the system so as to enable the temperature sensing system and/or the probe to be portable.

Figure 20:
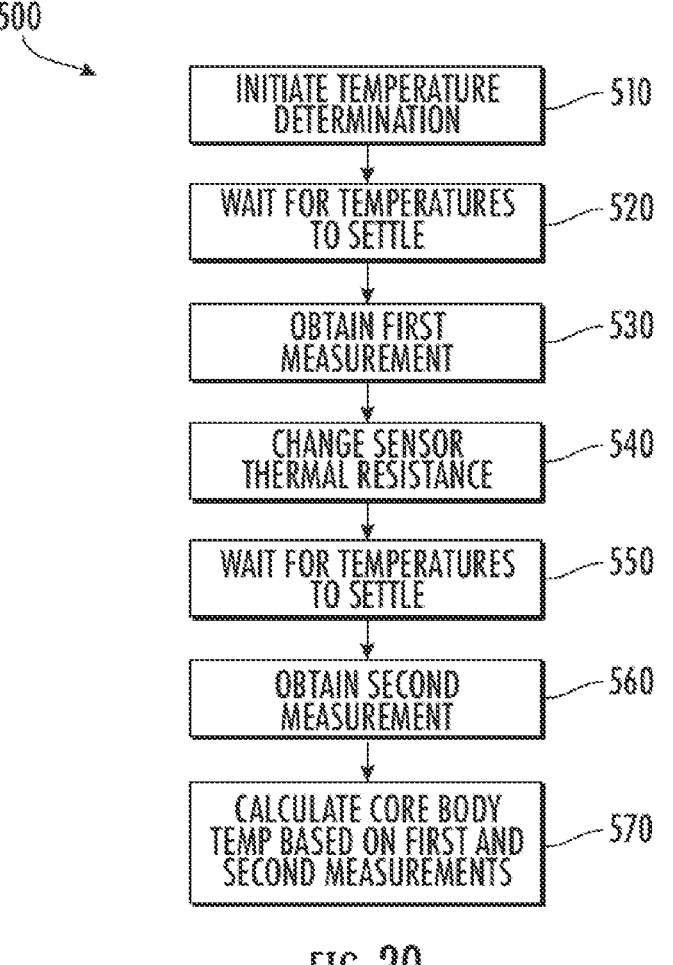
FIG. 20 depicts a flow diagram of a method of determining body core temperature of a subject using one of the temperature probe arrangements of FIGS. 3-5, 7-10, and 13-18.

FIG. 20 illustrates a process 500 for determining the body core temperature of a subject using one of the sensors 200, 200A, 200B, 240, 240A, 240B, 300, 300A, 340 described above. In the description of the method, statements that a method is performing some task or function refers to a controller or general purpose processor executing programmed instructions stored in non-transitory computer readable storage media operatively connected to the controller or processor to manipulate data or to operate one or more components in the sensors 200, 200A, 200B, 240, 240B, 300, 300A, 340, or the temperature sensing system 400 to perform the task or function. Particularly, the processor 408 of the temperature sensing system 400 described above may be such a controller or processor. Alternatively, the controller or processor may be implemented with more than one processor and associated circuitry and components, each of which is configured to form one or more tasks or functions described herein. It will be appreciated that some or all of the operations the method can also be performed by a remote server or cloud processing infrastructure. Additionally, the steps of the methods may be performed in any feasible chronological order, regardless of the order shown in the figures or the order in which the steps are described.

The process 500 begins by initiating the core body temperature determination (block 510). The temperature determination may be automatically initiated when the temperature probe is placed against the subject's skin. Alternatively, the temperature may be performed in response to a user input or at a prespecified time or at prespecified time intervals.

Once the temperature determination has begun, the process 500 proceeds with waiting for the temperatures of the one or more sensors of the temperature probe to settle or equalize to stable values (block 520). The processor may be configured to wait a specified time for the temperatures to settle, or the processor may be configured to monitor the signals corresponding to the temperature readings from the sensor(s) until the values are stable.

Next, the processor obtains a first temperature measurement from the temperature probe (block 530). The first temperature measurement includes temperature readings from the interface at the skin surface and the temperature reading on the opposite side of the insulator from the skin surface. As discussed in detail above, the two temperature measurements may be taken by separate temperature sensors in the temperature probe, or by a single Doppler sensor in the temperature probe.

The processor then operates the sensor to change the thermal resistance in the temperature probe (block 540). The processor changes the thermal resistance by, for example, applying a voltage to the piezoelectric element 244 in the temperature probe so as to cause the piezoelectric element 244 to expand or contract, thereby compressing or allowing expansion of the compressible elements in the temperature probe. Alternatively, the processor may operate to apply a signal to the MEMS switch 304, 304A so as to cause the MEMS switch 304, 304A to deform, or to apply a current to the fuses 348 so as to destroy or partially destroy at least one fuse 348.

After waiting for the temperatures to settle again in a similar manner as in block 520 (block 550), the processor operates the temperature probe to obtain a second temperature measurement (block 560). As in the first temperature measurement (block 530), the second temperature measurement includes temperature readings from the interface at the skin surface and the temperature reading on the opposite side of the insulator from the skin surface.

Finally, the processor determines the body core temperature based on the first and second temperature measurements using the dual flux equation (block 570):

$$T_B = T_1 + \frac{(T_1 - T_2)(T_1 - T_3)}{K(T_2 - T_4) - (T_1 - T_2)},$$

wherein $$K = \frac{R_1}{R_2}.$$

The first measurement obtains values for $T_1$ at the skin surface and $T_3$ on the opposite side of the insulator from the skin surface, while the second measurement obtains values for $T_2$ at the skin surface and $T_4$ at the opposite side of the insulator from the skin surface. The initial thermal resistance ($R_1$) and the changed thermal resistance ($R_2$) are known, or the ratio of the thermal resistances ($K$) is known, based on the design of the sensor device and the properties thereof. As a result, the body core temperature ($T_B$) can be calculated and displayed for a user or stored in the memory of the processor.

The disclosed sensor arrangements enable use of the dual heat flux method with only one Doppler temperature sensor or two individual temperature sensors necessary. As a result, a smaller and cheaper implementation of the system is possible. Moreover, the disclosed sensor arrangements provide improved sensor accuracy because, since the temperature readings are performed on the same portion of skin, the requisite assumption that the skin layers below the sensors are the same is necessarily satisfied.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the foregoing disclosure.

What is claimed is:

1. A temperature sensing system comprising:
an insulator having a thermal resistance that is controllable from a first thermal resistance to a second thermal resistance, the insulator including a plurality of fuses and a plurality of structures with low thermal conductivity relative to the fuses, the plurality of fuses and plurality of structures with lower thermal conductivity arranged in parallel with one another;
at least one temperature sensor operable to sense temperature at a first side and a second side of the insulator; and
a processor configured to control the thermal resistance of the insulator to change from the first thermal resistance to the second thermal resistance by applying a current to at least one of the plurality of fuses so as to at least partially destroy the at least one of the plurality of fuses.

2. The temperature sensing system of claim 1, wherein the processor is further configured to determine a subject core body temperature based on:
first detected temperatures from the at least one temperature sensor on the first side and the second side of the insulator when the insulator is at the first thermal resistance, and
second detected temperatures from the at least one temperature sensor on the first side and the second side of the insulator when the insulator is at the second thermal resistance.

3. The temperature sensing system of claim 2, wherein the processor is further configured to generate an output of the subject core body temperature as one of a perceptible output and an output signal.

4. The temperature sensing system of claim 3, wherein determination of the subject core body temperature is determined according to the equation:

$$T_B = T_1 + \frac{(T_1 - T_2)(T_1 - T_3)}{K(T_2 - T_4) - (T_1 - T_2)},$$

wherein:
$T_B$ is the subject core body temperature;
$T_1$ is the first detected temperature at the first side of the insulator;
$T_2$ is the second detected temperature at the first side of the insulator;
$T_3$ is the first detected temperature at the second side of the insulator;
$T_4$ is the second detected temperature at the second side of the insulator; and K is the first thermal resistance divided by the second thermal resistance.

5. The temperature sensing system of claim 1, wherein the at least one temperature sensor includes a Doppler sensor.

6. The temperature sensing system of claim 1, wherein the at least one temperature sensor includes a first temperature sensor on the first side of the insulator, and a second temperature sensor on the second side of the insulator.

7. The temperature sensing system of claim 1, wherein the processor is further configured to, in a subsequent temperature measurement, at least partially destroy at least one further fuse of the plurality of fuses so as to change the thermal resistance of the insulator in the subsequent temperature measurement.

\* \* \* \* \*